(12) United States Patent
Sevenster

(10) Patent No.: US 11,817,183 B2
(45) Date of Patent: Nov. 14, 2023

(54) PHENOTYPE ANALYSIS SYSTEM AND METHOD

(71) Applicant: KONINKLIJKE PHILIPS N.V., Eindhoven (NL)

(72) Inventor: Merlijn Sevenster, Haarlem (NL)

(73) Assignee: Koninklijke Philips N.V., Eindhoven (NL)

( * ) Notice: Subject to any disclaimer, the term of this patent is extended or adjusted under 35 U.S.C. 154(b) by 961 days.

(21) Appl. No.: 16/559,673

(22) Filed: Sep. 4, 2019

(65) Prior Publication Data

US 2020/0082915 A1    Mar. 12, 2020

Related U.S. Application Data

(60) Provisional application No. 62/729,488, filed on Sep. 11, 2018.

(51) Int. Cl.
*G16H 10/60* (2018.01)
*G16B 50/10* (2019.01)

(52) U.S. Cl.
CPC ............ *G16B 50/10* (2019.02); *G16H 10/60* (2018.01)

(58) Field of Classification Search
CPC ................................ G16H 10/60; G16B 50/10
See application file for complete search history.

(56) References Cited

U.S. PATENT DOCUMENTS

| | | | |
|---|---|---|---|
| 8,527,291 B1* | 9/2013 | Kochendorfer | G16H 70/60 705/2 |
| 2004/0128282 A1* | 7/2004 | Kleinberger | G06F 16/9535 |
| 2005/0149496 A1* | 7/2005 | Mukherjee | G06F 16/24575 |
| 2006/0052945 A1 | 3/2006 | Rabinowitz et al. | |
| 2006/0155693 A1* | 7/2006 | Chowdhury | G06F 16/951 |
| 2006/0288001 A1* | 12/2006 | Costa | G06F 16/951 707/999.005 |
| 2008/0120296 A1 | 5/2008 | Kariathungal et al. | |
| 2009/0125540 A1* | 5/2009 | Dettinger | G06F 16/2471 707/999.102 |
| 2010/0057675 A1* | 3/2010 | White | G06Q 30/02 707/E17.108 |
| 2011/0040765 A1 | 2/2011 | Presland | |
| 2012/0035954 A1* | 2/2012 | Yeskel | G16H 10/60 705/3 |
| 2013/0007040 A1* | 1/2013 | John | G06F 16/2471 707/769 |

(Continued)

OTHER PUBLICATIONS

Article entitled "LaneConnex: An Integrated Biomedical Digital Library Interface" by Ketchell et al., dated Mar. 2009 (Year: 2009).*

(Continued)

*Primary Examiner* — Mahesh H Dwivedi

(57) ABSTRACT

Phenotype analysis systems and methods. The methods described herein may involve receiving a phenotype query related to at least one phenotype of a patient. A processor executing instructions stored on memory may then select at least one of a first phenotype engine provided by a first entity and a second phenotype engine provided by a second entity to execute the received query on medical data associated with the patient. An interface may then output a result in response to the received phenotype query from at least one of the first and second phenotype engines.

18 Claims, 3 Drawing Sheets

(56) References Cited

U.S. PATENT DOCUMENTS

| | | | |
|---|---|---|---|
| 2014/0046926 A1* | 2/2014 | Walton | G16H 10/20 |
| | | | 707/710 |
| 2015/0006558 A1 | 1/2015 | Leighton et al. | |
| 2015/0073943 A1* | 3/2015 | Norris | G16H 40/20 |
| | | | 705/26.63 |
| 2016/0019299 A1 | 1/2016 | Boloor et al. | |
| 2016/0026666 A1* | 1/2016 | Namiki | G06F 16/2255 |
| | | | 707/744 |
| 2017/0053064 A1* | 2/2017 | Bhavani | G06F 16/5866 |
| 2017/0177675 A1* | 6/2017 | Beller | G06N 3/004 |
| 2017/0213001 A1* | 7/2017 | Harrison | G16H 40/63 |
| 2017/0270212 A1* | 9/2017 | Lavrenko | G16B 50/40 |
| 2017/0329872 A1* | 11/2017 | Dispensa | G06F 16/24522 |
| 2020/0394197 A1* | 12/2020 | Gutfreund | G06F 16/951 |

OTHER PUBLICATIONS

Article entitled "Building an Open Source Meta-Search Engine", by Gulli et al., dated May 14, 2005 (Year: 2005).*

Article entitled "PhenomicDB: A Multi-Species Genotype/Phenotype Databse for Comparative Phenomics" by Kahraman et al., dated 2004 (Year: 2004).*

Article entitled "MetaSeek: a content-based metasearch engine for images", by Beigi et al., dated Dec. 23, 1997 (Year: 1997).*

Article entitled "The Metacrawler architecture for resource aggregation on the web", by Selburg et al., dated Feb. 1997. (Year: 1997).*

Article entitled "A Survey on Meta Search Engine in Semantic Web", by Sudeepthi et al., dated 2011 (Year: 2011).*

* cited by examiner

PHENOTYPE ANALYSIS SYSTEM AND METHOD

TECHNICAL FIELD

Embodiments described herein generally relate to phenotype analysis systems and methods.

BACKGROUND

Electronic medical records (EMRs) provide the de facto ground truth for patient information. An EMR's presentation of patient data is primarily organized by data type. For example, lab values may be organized into one panel or section of a display under a "lab values list", chronic conditions may be listed in a "problem list," active drugs may be listed under a "medication list," etc.

Physicians and other types of clinical workers have generally developed heuristics for searching for information based on how data is organized in the EMR. For instance, if a clinician needs to know whether a patient is diabetic, they may first consult the problem list. If a diabetes code or some other indicia indicating the patient has diabetes is present, the clinician may determine the patient is diabetic.

If, on the other hand, no diabetes code is found, the clinician may then consult the medication list for certain medications (e.g., insulin). If no such medications are listed, the clinician may then check the recent lab values for A1c values.

However, there is no single, controlled field in the EMR that reflects the current/up-to-date status of a given phenotype such as diabetes. Accordingly, clinicians cannot simply query for a phenotype status for a given patient.

A need exists, therefore, for systems and methods that overcome the disadvantages of existing medical record analysis techniques.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

According to one aspect, embodiments relate to a phenotype analysis system. The system includes an interface for receiving a phenotype query from a user, wherein the received phenotype query is related to at least one phenotype of a patient, at least one database storing medical data associated with the patient, and a processor executing instructions stored on a memory to provide a phenotype engine array that includes at least a first phenotype engine provided by a first entity and a second phenotype engine provided by a second entity, wherein at least one of the first and second phenotype engines execute the received phenotype query on the medical data associated with the patient and provide a result in response to the received phenotype query.

In some embodiments, the interface is further configured to receive instructions regarding which phenotype engines are to execute the received phenotype query. In some embodiments, the instructions include a performance metric specified by the user.

In some embodiments, the processor is further configured to analyze ontological phenotypes related to the received phenotype query, and select at least one phenotype engine to execute the received phenotype query based on the ontological phenotypes related to the received phenotype query.

In some embodiments, the processor is further configured to collect data used by at least the first and second phenotype engines, wherein phenotype engines that require data not in the medical data associated with the patient do not execute the received phenotype query.

In some embodiments, at least the first phenotype engine includes a plurality of sub-engines that are each configured to analyze the medical data associated with the patient in a predetermined way to execute the received phenotype query.

In some embodiments, the phenotype engine array includes a plurality of phenotype engines provided by one or more entities, wherein at least two of the phenotype engines are provided by different entities and execute queries regarding different phenotypes.

In some embodiments, the first entity and the second entity are the same entity.

According to another aspect, embodiments relate to a method for operating a phenotype analysis system. The method includes receiving, using an interface, a phenotype query from a user, wherein the received phenotype query is related to at least one phenotype of a patient; selecting, using a processor executing instructions stored on a memory, at least one of a first and a second phenotype engine to execute the received phenotype query on medical data associated with the patient; and outputting, using the interface, a result in response to the received phenotype query from at least one of the first and second phenotype engines.

In some embodiments, the method further includes receiving, using the interface, instructions regarding which phenotype engines are to execute the received phenotype query. In some embodiments, the instructions include a performance metric specified by the user.

In some embodiments, the method further includes analyzing, using the processor, ontological phenotypes related to the received phenotype query; and selecting, using the processor, at least one phenotype engine to execute the received query based on the ontological phenotypes related to the received phenotype query.

In some embodiments, the method further includes collecting, using the processor, data used by at least the first and second phenotype engines, wherein phenotype engines that require data not in the medical data associated with the patient do not execute the received phenotype query.

In some embodiments, at least the first phenotype engine includes a plurality of sub-engines that are each configured to analyze the medical data associated with the patient in a predetermined way to execute the received phenotype query.

In some embodiments, the phenotype engine array includes a plurality of phenotype engines provided by one or more entities, wherein at least two of the phenotype engines are provided by different entities and execute queries regarding different phenotypes.

According to yet another aspect, embodiments relate to a non-transitory computer-readable medium containing computer executable instructions for performing a method for operating a phenotype analysis system. The computer-readable medium includes computer-executable instructions for receiving, at a phenotype engine array, a first phenotype engine provided by a first entity; computer-executable instructions for receiving, at the phenotype engine array, a second phenotype engine provided by a second entity; computer-executable instructions for receiving, using an interface, a phenotype query from a user, wherein the received phenotype query is related to at least one phenotype of a patient; computer-executable instructions for selecting, using a processor executing instructions stored on a memory, at least one of the first and second phenotype engines to execute the received phenotype query on medical data associated with the patient; and computer-executable instructions for outputting, using the interface, a result in response to the received phenotype query from at least one of the first and second phenotype engines.

BRIEF DESCRIPTION OF DRAWINGS

Non-limiting and non-exhaustive embodiments of the embodiments herein are described with reference to the following figures, wherein like reference numerals refer to like parts throughout the various views unless otherwise specified.

DETAILED DESCRIPTION

Figure 1:
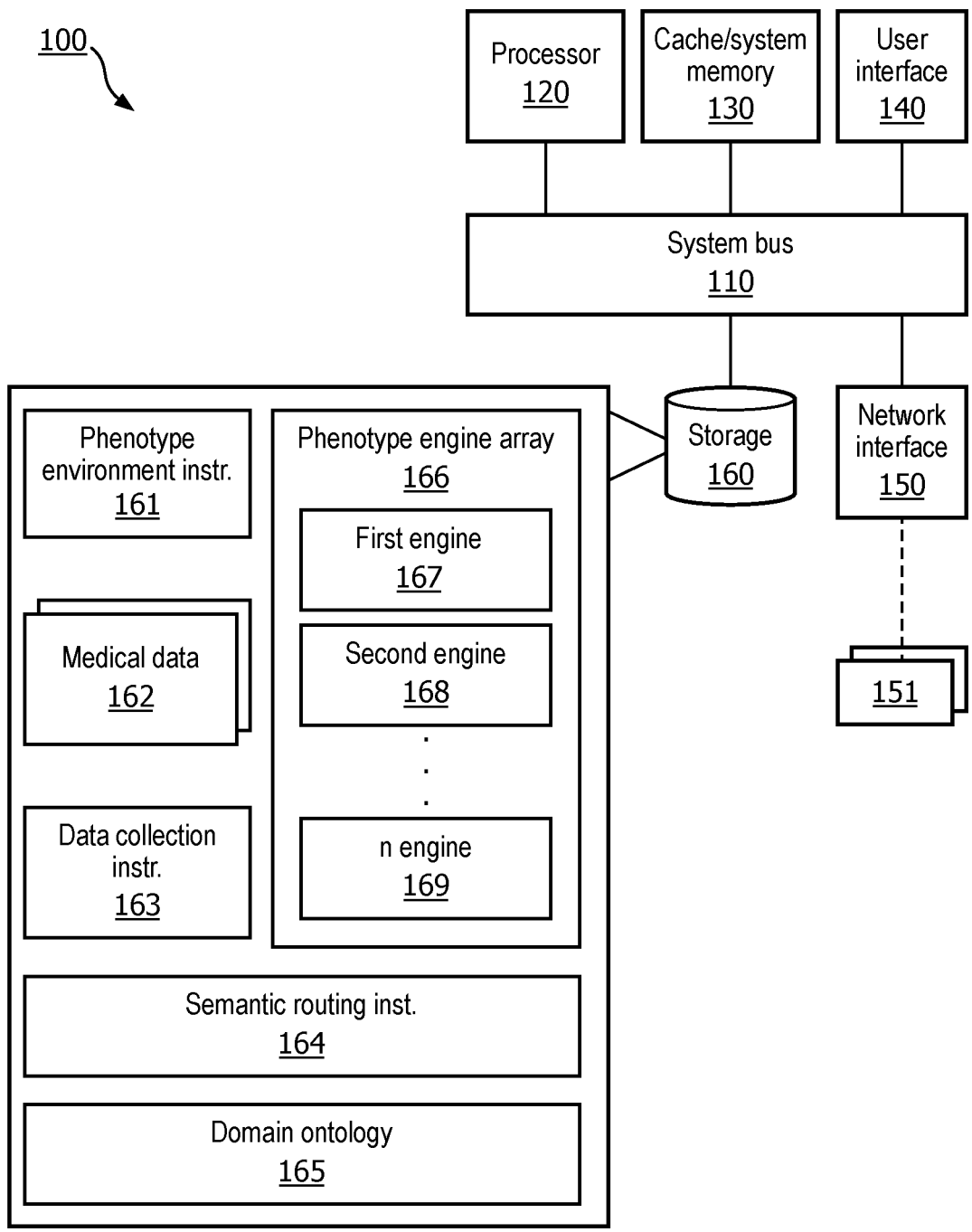
FIG. 1 illustrates a phenotype analysis system in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

As discussed previously, a shortcoming of existing techniques for viewing and analyzing patient data is that there is no single, controlled field that reflects the current or up-to-date status of a given phenotype. As a result, a clinician cannot simply query the patient data to obtain a phenotype status of a given patient.

Recently, however, studies have shown that phenotype statuses can be realistically and accurately derived from heterogeneous types of patient data. For instance, the following rule can be implemented to detect diabetes:

If one of the following holds, diabetes=true:
(i) There is a diabetes code in the "problem list"—OR—

(ii) There is an insulin drug on the medication list—OR—
(iii) There is a recent A1c lab value equal to or greater than 7%.

Accordingly, the systems and methods described herein enable the automated phenotyping of arbitrary clinical phenotypes based on a set of phenotyping rules executed by one or more phenotyping engines. In accordance with the systems and methods described herein, third parties may develop and provide their own phenotyping engines for clinician use.

FIG. 1 illustrates a phenotype analysis system 100 in accordance with one embodiment. The processor 120 may be any hardware device capable of executing instructions stored on memory 130 or in storage 160 or otherwise capable of processing data. As such, the processor 120 may include a microprocessor, field programmable gate array (FPGA), application-specific integrated circuit (ASIC), or other similar devices.

In some embodiments, such as those relying on one or more ASICs, the functionality described as being provided in part via software may instead be configured into the design of the ASICs and, as such, the associated software may be omitted. The processor 120 may be configured as part of a user device on which a user interface 140 executes, such as a laptop, or may be located at some remote location.

The memory 130 may include various memories such as, for example L1, L2, or L3 cache or system memory. As such, the memory 130 may include static random access memory (SRAM), dynamic RAM (DRAM), flash memory, read only memory (ROM), or other similar memory devices. The exact configuration of the memory 130 may vary as long as instructions for operating the phenotype analysis system 100 can be executed.

The user interface 140 may execute on one or more devices for enabling communication with a user such as a clinician or other type of medical personnel. For example, the user interface 140 may include a display, a mouse, and a keyboard for receiving user commands. In some embodiments, the user interface 140 may include a command line interface or graphical user interface that may be presented to a remote terminal via the network interface 150.

The user interface 140 may execute on a user device such as a PC, laptop, tablet, mobile device, smartwatch, or the like. The exact configuration of the user interface 140 and the device on which it executes may vary as along as the features of various embodiments described herein may be accomplished.

The network interface 150 may include one or more devices for enabling communication with other hardware devices. For example, the network interface 150 may include a network interface card (NIC) configured to communicate according to the Ethernet protocol. Additionally, the network interface 150 may implement a TCP/IP stack for communication according to the TCP/IP protocols. Various alternative or additional hardware or configurations for the network interface 150 will be apparent.

The network interface 150 may be in operable communication with one or more entities 151 to enable the entities to provide their own phenotype engines. That is, entities such as companies or individuals may create their own engines for upload to the system 100.

Operators of the system 100 may for provide payment in exchange for an entity's uploaded engine. This payment include a one-time, upfront payment or continuing (e.g., monthly) payments in order for the system 100 to continue to host the provided engine(s).

Operators of the system 100 can then charge users (e.g., clinicians) each time they rely on a phenotype engine for a query. The operators can then split this payment with the entities that provided the used phenotype engines in accordance with any applicable agreements between the operators of the system 100 and the entities that provided the used phenotype engines.

Accordingly, the system 100 may operate as a marketplace in which entities may create and upload their own phenotype engines directed towards some type of phenotype. Clinicians may then query these engines by accessing the system 100 to obtain some type of phenotype status regarding a patient.

The entities 151 may be in communication with the system 100 over one or more networks that may link the various components with various types of network connections. The network(s) may be comprised of, or may interface to, any one or more of the Internet, an intranet, a Personal Area Network (PAN), a Local Area Network (LAN), a Wide Area Network (WAN), a Metropolitan Area Network (MAN), a storage area network (SAN), a frame relay connection, an Advanced Intelligent Network (AIN) connection, a synchronous optical network (SONET) connection, a digital T1, T3, E1, or E3 line, a Digital Data Service (DDS) connection, a Digital Subscriber Line (DSL) connection, an Ethernet connection, an Integrated Services Digital Network (ISDN) line, a dial-up port such as a V.90, a V.34, or a V.34bis analog modem connection, a cable modem, an Asynchronous Transfer Mode (ATM) connection, a Fiber Distributed Data Interface (FDDI) connection, a Copper Distributed Data Interface (CDDI) connection, or an optical/DWDM network.

The network or networks may also comprise, include, or interface to any one or more of a Wireless Application Protocol (WAP) link, a Wi-Fi link, a microwave link, a General Packet Radio Service (GPRS) link, a Global System for Mobile Communication G(SM) link, a Code Division Multiple Access (CDMA) link, or a Time Division Multiple access (TDMA) link such as a cellular phone channel, a Global Positioning System (GPS) link, a cellular digital packet data (CDPD) link, a Research in Motion, Limited (RIM) duplex paging type device, a Bluetooth radio link, or an IEEE 802.11-based link.

The storage 160 may include one or more machine-readable storage media such as read-only memory (ROM), random-access memory (RAM), magnetic disk storage media, optical storage media, flash-memory devices, or similar storage media. The storage 160 may include phenotype environment instructions 161, medical data associated with the patient 162, data collection instructions 163, semantic routing instructions 164, domain ontology(ies) 165, and a phenotype engine array 166. The phenotype engine array 16 may execute a plurality of phenotype engines 167, 168, 169, etc. provided by one or more entities 151. As discussed below, each of the engines may execute one or more sub-engines.

The medical data associated with the patient 162 may include one or more records related to some aspect of a patient's health. The medical data associated with the patient 162 may include demographic information related to the patient such as their age, gender, or weight, as well as information related to their medical history such as previous test results and prescribed medications. The medical data associated with the patient 162 may be stored as part of a patient's electronic medical record (EMR).

The data collection instructions 163 may cause the processor 120 to consult the medical data associated with the patient 162 to retrieve certain types of patient data. As discussed below, the type of data retrieved may depend on the rules executed by the applicable phenotype engines.

The semantic routing instructions 164 may cause the processor 120 to consider structured domain knowledge regarding one or more domain ontologies 165 to recognize the significance of words or phrases in the phenotype query. Specifically, by executing the semantic routing instructions 164, the processor 120 may mediate between phenotype queries from the phenotype environment and engines in the phenotype engine array 166. The one or more domain ontologies 165 may store data regarding various ontologies. For example, the domain ontology 165 may include SNOMED CT or any other appropriate ontology.

The phenotype engine array 166 may execute or otherwise include one or more phenotype engines to analyze a received phenotype query. As discussed below, these engines may be configured to analyze any one of a variety of phenotypes and may be provided by one or more entities.

Figure 2:
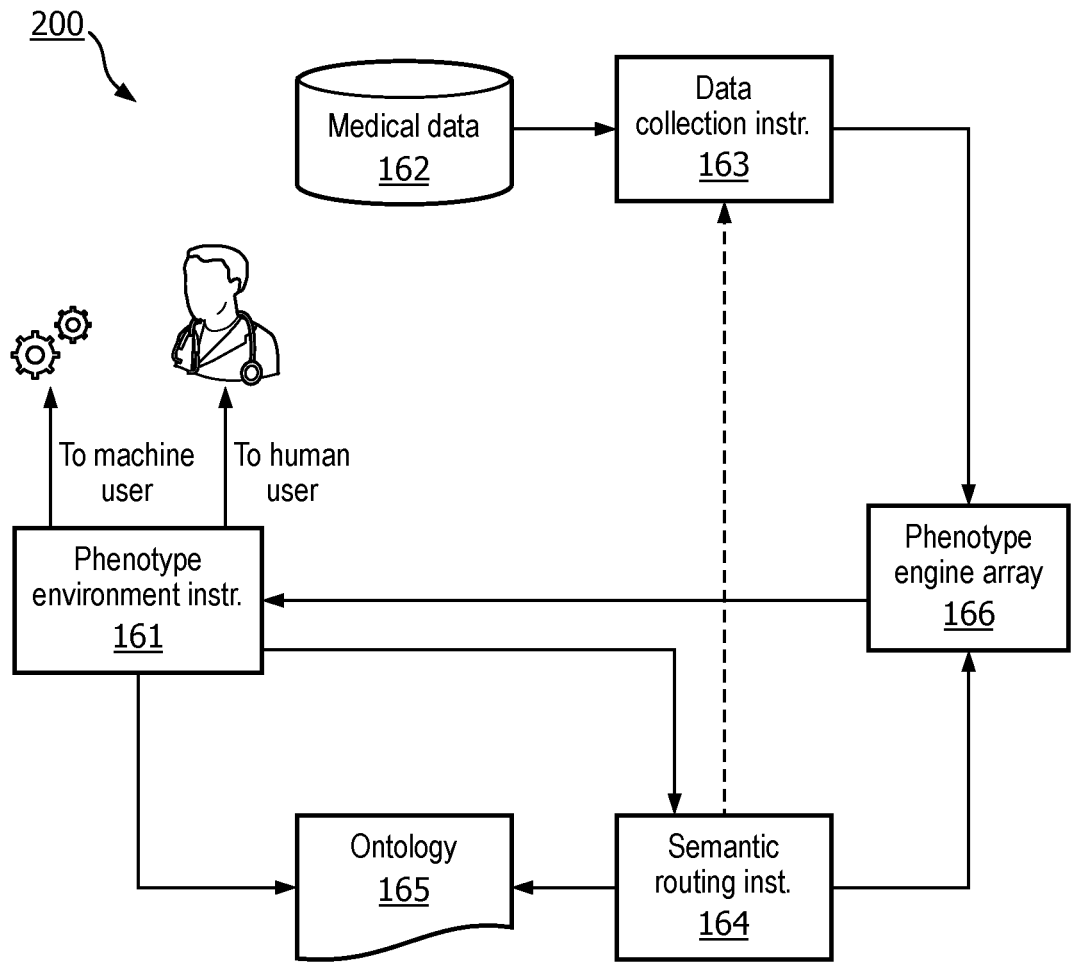
FIG. 2 illustrates an exemplary workflow of the components of the system of FIG. 1 in accordance with one embodiment.

FIG. 2 illustrates a workflow 200 of operating a phenotype analysis system such as the system 100 of FIG. 1 in accordance with one embodiment. This workflow 200 shows how the components of FIG. 1 operate in conjunction with each other to respond to a received phenotype query.

The processor 120 may, by executing the phenotype environment instructions 161, present a phenotype environment using a user interface that allows a user to specify relevant phenotypes and input phenotype queries. The presented phenotype environment may also display results to queries to a user.

The phenotype environment may present, for example, a drop-down list specifying multiple phenotypes or clinical conditions. This list can include an extensive set of clinical conditions based on an ontology such as SNOMED CT or the International Statistical Classification of Diseases and Related Health Problems ("ICD"). In this manner, a user can input a phenotype query by selecting "diabetes" or "metabolic disease," for example.

Additionally, a user can input instructions regarding which phenotype engine(s) are to execute the received phenotype query. The user can also specify how query results are presented. For instance, the output can be presented as a yes/no result (e.g., whether the patient has a condition), a normal/mild/moderate/severe result relating to the severity of the patient's condition, a numerical value, or the like.

The user can also configure the phenotype environment to present a confidence/certainty value associated with a returned result. For example, the confidence/certainty value may be expressed on a scale from 0 to 1, with a value of "0" indicating low confidence in the returned result and a value of "1" indicating high confidence.

The confidence level may ultimately depend on the quality of the phenotype engine that executed the phenotype query. That is, two or more phenotype engines could be selected to analyze the same phenotype query, but one of the phenotype engines is able to provide a higher confidence value than another engine.

The phenotype environment may also specify the data sources that need to be searched, at minimum, for a particular phenotype engine. For example, a phenotype engine that determines whether a patient has diabetes may require, at minimum, a problem list, a medication list, and laboratory results. This may help a user select the most appropriate phenotype engine(s) to execute a phenotype query based on the engines' requirements and the available data.

This feature may be useful in situations in which a patient is very ill, but the patient is new to a network or otherwise visiting a particular healthcare institution for the first time. In these cases, the medical data associated with the patient may be incomplete. For example, the problem list and the medication list may be empty or otherwise incomplete.

The phenotype environment may therefore inform a user that a particular phenotype engine requires data from the medication list and/or the problem list in order to provide a result. The user interface 140 may present this information so the user is aware that this particular phenotype engine should not be selected.

The phenotype environment may enable more complicated pre-checks as well. For example, the phenotype environment may check not only whether a particular data source is complete, but also whether the data source has been updated within a month or some predetermined time period.

Similarly, the phenotype environment executed by the user interface 140 may, in addition to providing a result to a received phenotype query, provide the data the selected phenotype engine(s) relied on in reaching the result. For example, the user interface 140 may present the source document(s) on which the result was based.

A user may also specify whether the output needs to be confirmed by a human user before it is exported. This decision may be dependent on the certainty of the analysis. That is, query results with low certainty or confidence may require human confirmation.

The user interface 140 presenting the phenotype environment may simply act as an in-between that receives the assessment from one or more phenotype engines and writes the data into a structured object in, for example, eXtensible Markup Language (XML) or JavaScript Object Notation (JSON). This electronic object may then be used by downstream applications and/or to populate a registry of patient information.

The processor 120 may then execute the semantic routing instructions 164 to initiate the phenotype search. The semantic routing instructions 164 may cause the processor 120 to recognize the semantic significance of phrases or words that are part of the phenotype query based on one or more ontologies 165.

The processor 120, when executing the semantic routing instructions 164, may recognize a hierarchical structure among the codes of an ontology 165 to determine the appropriate phenotype engine(s) based on semantic reasoning. For instance, if there is a request to search for diabetes, and there is a phenotype engine to analyze diabetes, then this engine will be eligible for conducting the search. The semantic routing instructions 164 may cause the processor 120 to check which data sources are available to assess eligibility, too.

A more complex scenario may involve a phenotype query relating to "metabolic disease." In this case, the diabetes phenotype engine will still be eligible because diabetes is a type of metabolic disease. Accordingly, the processor 120 may consider the hierarchical relationships between conditions and other phrases associated with a received phenotype query.

In this manner, the following exemplary semantic routing instructions 164 can be followed to determine eligible phenotype engines:

Let E be an empty set;
Let C be the ICD code of the requested phenotype;
For each ICD code D, do:

Add D to E if D is hierarchically subordinate or equal to E;

Return E.

For example, "C" may be an ICD code for cancer. Any codes D that are associated with, for example, a particular type of cancer (e.g., lung cancer, breast cancer, etc.) would then be added to the set E. Phenotype engines associated with the codes D in the set E may then be selected to execute the received phenotype query.

Referring back to FIG. 2, the medical data associated with the patient 162 may provide a repository of patient data. The medical data associated with the patient 162 may be queried by the selected phenotype engine(s) for analysis. Each patient may be associated with a particular unique patient identifier, for example.

Specifically, the processor 120 may execute the data collection instructions 163 to retrieve medical data associated with the patient 162 that is required by one or more phenotype engines. In some embodiments, a phenotype engine may require select document types (e.g., only the problem list, the medication list, and recent laboratory results). The medical data associated with the patient 162 may be returned in a structured format, such as a format that conforms to the Clinical Document Architecture (CDA) standard.

The phenotype engine array 166 may include a plurality of phenotype engines. These engines may include engines created to analyze a particular phenotype and may be provided by one or more entities.

The phenotype engine array 166 may include a plurality of phenotype engines that are designed to analyze the same phenotype. In this case, the system 100 provides a competitive marketplace in which users may select a particular engine based on its quality, applicability, cost, accuracy, speed, or some other type of metric such as the reputation of the entity that provided the particular engine.

The system 100 may also provide a rating system for users to rate the phenotype engines they have used. Accordingly, users may consider this data in selecting the most appropriate phenotype engine(s). Users may also provide comments sharing their experience(s) with particular phenotype engines so that future, potential users of certain phenotype engines may have a better idea of what to expect if/when using a particular phenotype engine. This data related to the review of the phenotype engines may be stored in one or more databases and also as part of an engine's profile (discussed below).

For organizational purposes, each phenotype engine may be tagged with a particular code to identify the phenotype that it analyzes. These codes may be ICD codes, for example. Accordingly, when an entity provides a phenotype engine, the entity may also label the phenotype engine with a particular ICD code. On the user side, a user may search for relevant phenotype engines by inputting the ICD code when providing a query.

Entities may configure or otherwise create their engines in a variety of ways. For example, engines may be implemented based on rules, statistical models, machine learning techniques, natural language processing/concept extraction methods, or the like.

Each engine may execute multiple sub-engines that each analyze different types of medical data associated with the patient. Additionally or alternatively, sub-engines of a particular phenotype engine may analyze the same data source, but in a different way.

In this manner, a diabetes phenotype engine may have three sub-engines: one sub-engine executing rules for detecting the diabetes ICD code on the problem list, one sub-engine executing rules for detecting insulin on the medication list, and one sub-engine executing rules for detecting an elevated A1c laboratory result. This particular phenotype engine may then combine the outcome of these sub-engines in a sensible manner. For example, the phenotype engine may rely on a Boolean combination (e.g., if two of the sub-engines return a positive result, then the engine may conclude the patient has diabetes). Additionally or alternatively, the output from the sub-engines may be weighted based on manual input.

For example, weights may be assigned based on various clinician preferences or strategies. Oftentimes clinicians may have their own internal strategies that they implement when reviewing patient data. This data may be weighted based, on for example, the person who gathered a particular patient measurement (e.g., their expertise or seniority level) when analyzing the patient data.

Entities may be required to provide a phenotype engine profile for their provided engines that specify how their phenotype engines generally operate. The level of detail required may vary and may include the data source(s) on which the engine operates. A phenotype engine's profile may also include the engine's outcome value type (e.g., yes/no, normal/mild/moderate/severe, a numerical value, a percentage, a color-coded indicia, etc.). The profile may also specify the minimal data sources ingested or otherwise required by the engine, and the maximum data sources (e.g., medication list, laboratory results, etc.).

As mentioned previously, the engine(s) may return a confidence or certainty value (e.g., in the range of 0 to 1) as well as the data source(s) relied upon in making a determination. The engine(s) may also provide certain data that motivates the outcome. For instance, in the case of diabetes, a source document could be a problem list and the "motivating element" could be the presence of the ICD code indicating diabetes. Similarly, in the case of congestive heart failure (CHF), the source document could be a physical note and the motivating element may be a sentence confirming that the patient has severe CHF.

Preferably, each provided engine in the phenotype engine array 166 has been validated and provides performance metrics as part of its profile. Performance metrics may include, but are not limited to, sensitivity, specificity, positive predictive value (PPV), negative predictive value (NPV), accuracy, area under the receiver-operator curve (AUC), or the like. Each metric itself can have a confidence interval or multiple confidence intervals (e.g., a 90% confidence interval, a 95% confidence interval, etc.). Generally, the confidence interval may become narrower if an engine has been validated on more data.

The results obtained by the phenotype engine array 166 (i.e., by one or more engines included in the array 166) may then be presented to the user by the phenotype environment. If more than one engine executed the received phenotype query and provided a result, the user may compare the result(s) to make a more informed clinical decision. The provided results and data associated therewith may also be communicated to and stored in some machine readable medium such as in the patient's EMR.

Figure 3:
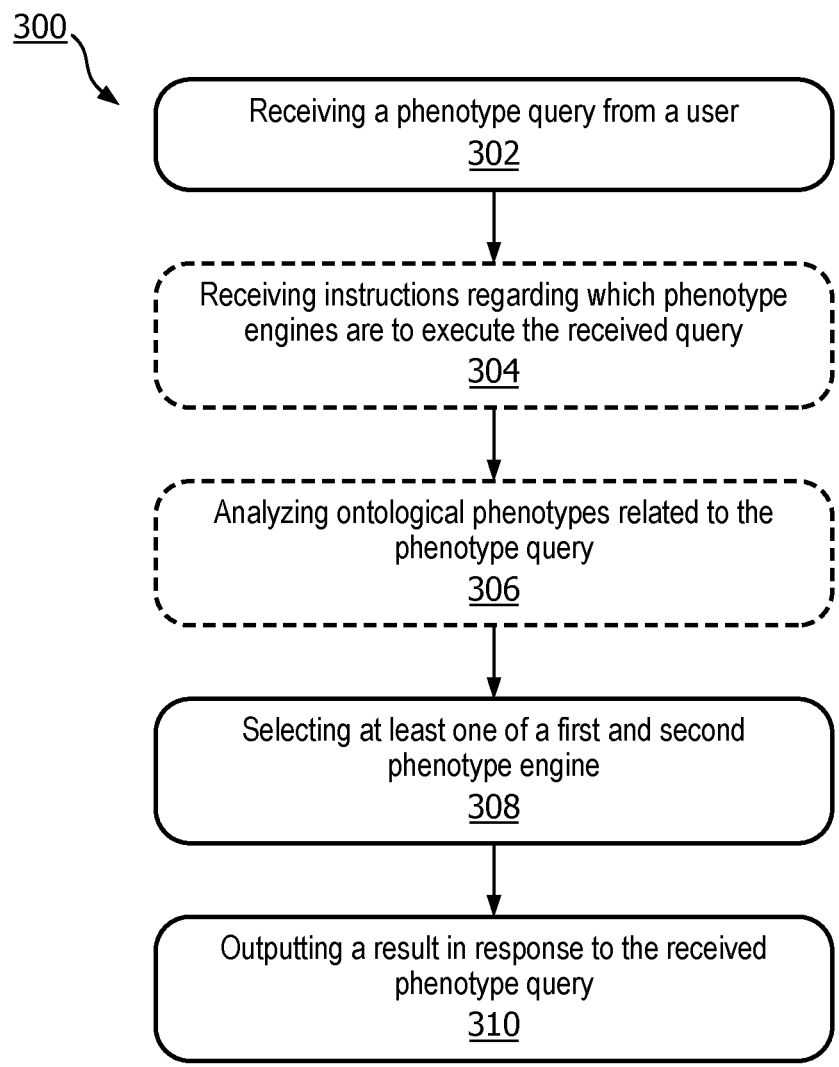
FIG. 3 depicts a flowchart of a method for operating a phenotype analysis system in accordance with one embodiment.

FIG. 3 depicts a flowchart of a method 300 for operating a phenotype analysis system in accordance with one embodiment. The phenotype analysis system may be similar to the system 100 of FIG. 1, for example.

Step 302 involves receiving, using an interface, a phenotype query from a user, wherein the received phenotype query is related to at least one phenotype of a patient. In this embodiment, the user may be a clinician or other type of medical personnel seeking the status of a particular phenotype of a particular patient. For example, the clinician may want to know whether a particular patient has diabetes. As another example, the clinician may want to know the severity of a particular medical condition of the patient.

Accordingly, the user may provide this query using any suitable interface such as the user interface 140 of FIG. 1. A user may, for example, provide some input with respect to the patient of interest, and then input or otherwise select some phenotype based on its ICD code.

Step 304 is optional and involves receiving, using the interface, instructions regarding which phenotype engine(s) are to execute the received phenotype query. The interface may be in communication with a phenotype engine array that includes one or more phenotype engines that are configured to analyze phenotype queries such as the query received in step 302. These phenotype engines may be created by the same or different entities. While these phenotype engines may be configured to analyze the same phenotype, they may be configured to do so differently.

For example, some phenotype engines may require different types of data for analyzing a phenotype. Or, some phenotype engines may have a higher degree of accuracy than others. As discussed above, each engine may be associated with a profile that tells the user about its operation.

Accordingly, a user may have the option of inputting additional parameters or requirements (i.e., instructions) associated with the query. For example, a user may specify that only phenotype engines that are capable of producing a result with a 95% or above accuracy rate should be used. As another example, a user may specify certain data that must considered in responding to a query. Accordingly, phenotype engines that do not consider, for example, patient medications will not be selected to analyze the received phenotype query.

A user may also affirmatively select one or more phenotype engines to analyze the query. For example, a clinician may have used a certain phenotype engine or may have used phenotype engines provided by a specific entity in the past and are therefore familiar with a particular engine/entity.

Step 306 is optional and involves analyzing, using the processor, ontological phenotypes related to the received phenotype query. For example, step 306 may involve analyzing the semantic relationships of words or phrases that are part of the received phenotype query based one on or more ontologies. If a received phenotype query includes the term "cancer", step 306 may involve recognizing that "lung cancer" is a relevant condition and therefore engines that analyze lung cancer should be selected.

Step 308 involves selecting, using a processor executing instructions stored on a memory, at least one of a first and a second phenotype engine to execute the received phenotype query on medical data associated with the patient. The processor may therefore consider any instructions from the user regarding which phenotype engine(s) are to analyze the received phenotype query. In addition to or lieu of considering instructions provided by the user, the processor may be configured to select one or more phenotype engines autonomously by considering data regarding previously executed queries regarding the phenotype, queries submitted by the particular user, or knowledge regarding which phenotype engine(s) are most suitable to respond to a particular type of query.

For example, the processor may execute semantic reasoning instructions to analyze the semantic meaning of the phenotype query and known ontologies (as discussed in step 306). With reference to the above hierarchical instructions, the processor may match the received requirements from the phenotype environment with the profiles of the phenotype engines.

For example, a received phenotype query may be accompanied by requirements such as the user specifying they want to research diabetes and want a response that meets certain criteria (e.g., an NPV above 30%). Accordingly, there is some minimum eligibility requirements that the phenotype engines need to satisfy in order to be eligible. Engines that have been provided by various entities therefore may or may not be eligible for selection. The processor therefore ensures there is a match between the requirements from the phenotype environment and the profiles of potentially applicable phenotype engines. This confirmation step may also ensure that the required medical data associated with the patient are available.

Once the set of eligible phenotype engines has been finalized, the processor may execute the data collection engine to obtain the required documents or other medical data associated with the patient. If the returned set of documents or otherwise the returned medical data associated with the patient is not sufficient for any of the phenotype engines, these engines may be eliminated as well. For instance, if the medical data associated with the patient only includes a problem list and a medication list, all phenotype engines with rules that minimally require laboratory results (or laboratory results dated within the previous 90 days, for example), are eliminated.

Step 310 involves outputting, using the interface, a result in response to the received phenotype query from at least one of the first and second phenotype engines. The result of each of the selected phenotype engine(s) may then be presented to a user so that the user can make an informed clinical decision. The output may relate to, for example, whether the patient has a medical condition or the severity of any such condition. The output may be presented to the user via any suitable means such as a visual message, an audio message, a haptic message, or some combination thereof. The result may then be stored in a database such as in the patient's EMR to be part of the medical data associated with the patient.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A phenotype analysis system, the system comprising:
   an interface configured to receive a phenotype query from a user for a phenotype status of at least one phenotype of a patient;
   at least one database storing medical data of the patient; and
   a processor executing instructions stored on a memory, wherein executing the instructions causes the processor to:
   select from a phenotype engine array at least a first phenotype engine provided by a first entity and a second phenotype engine provided by a second entity for executing the received phenotype query, based at least in part on semantic meaning of the received phenotype query, wherein the interface is further configured to receive minimum eligibility requirements of phenotype engines for executing the received phenotype query, and wherein the instructions cause the processor to select the first phenotype engine and the second phenotype engine further by matching the minimum eligibility requirements and profiles of the first phenotype engine and the second phenotype engine in the phenotype engine array;
   provide the first phenotype engine and the second phenotype engine, wherein each of the first phenotype engine and the second phenotype engine executes the received phenotype query on the medical data of the patient and provides results in response to the received phenotype query; and
   present a confidence value associated with the results from each of the first phenotype engine and the second phenotype engine to the user, wherein the results of the first phenotype engine or the second phenotype engine having a higher confidence value are selected.

2. The system of claim 1 wherein the first phenotype engine and the second phenotype engine are selected further based on corresponding predetermined performance metrics.

3. The system of claim 1 wherein the instructions further cause the processor to:
   analyze ontological phenotypes related to the received phenotype query; and
   select the first phenotype engine and the second phenotype engine to execute the received phenotype query further based on the ontological phenotypes related to the received phenotype query.

4. The system of claim 1 wherein the instructions further cause the processor to collect data used by at least the first and second phenotype engines, wherein phenotype engines in the phenotype engine array that require data not in the medical data stored in association with the patient are not selected to execute the received phenotype query.

5. The system of claim 1 wherein at least the first phenotype engine includes a plurality of sub-engines that are each configured to analyze the medical data stored in association with the patient in a predetermined way to execute the received phenotype query.

6. The system of claim 1, wherein the first entity and the second entity are the same.

7. A method for operating a phenotype analysis system, the method comprising:
   receiving, using an interface, a phenotype query from a user for a phenotype status of at least one phenotype of a patient;
   selecting from a phenotype engine array, using a processor executing instructions stored on a memory, at least a first phenotype engine provided by a first entity and a second phenotype engine provided by a second entity to execute the received phenotype query on medical data stored in association with the patient, based at least in part on semantic meaning of the phenotype query, wherein the interface is further configured to receive minimum eligibility requirements of phenotype engines for executing the received phenotype query, and wherein the instructions cause the processor to select the first phenotype engine and the second phenotype engine further by matching the minimum eligibility requirements and profiles of the first phenotype engine and the second phenotype engine in the phenotype engine array;
   outputting, using the interface, results in response to the received phenotype query from the first phenotype engine and the second phenotype engine;
   determining, using the processor executing instructions stored on the memory, a confidence value associated with the results from each of the first phenotype engine and the second phenotype engine to the user; and selecting the results of the first phenotype engine or the second phenotype engine having a higher confidence value.

8. The method of claim 7 wherein the first phenotype engine and the second phenotype engine are selected further based on corresponding predetermined performance metrics.

9. The method of claim 7 further comprising:
analyzing, using the processor, ontological phenotypes related to the received phenotype query; and
selecting, using the processor, the first phenotype engine and the second phenotype engine to execute the received phenotype query further based on the ontological phenotypes related to the received phenotype query.

10. The method of claim 7 further comprising collecting, using the processor, data used by at least the first and second phenotype engines, wherein phenotype engines in the phenotype engine array that require data not in the medical data stored in association with the patient are not selected to execute the received phenotype query.

11. The method of claim 7 wherein at least the first phenotype engine includes a plurality of sub-engines that are each configured to analyze the medical data stored in association with the patient in a predetermined way to execute the received phenotype query.

12. The method of claim 7 wherein the first phenotype engine and the second phenotype engine are provided by different entities.

13. A non-transitory computer-readable medium containing computer executable instructions for operating a phenotype analysis system, that when executed, the instructions cause a processor to:
receive, at a phenotype engine array, a plurality of phenotype engines including a first phenotype engine provided by a first entity and a second phenotype engine provided by a second entity;
receive, using an interface, a phenotype query from a user for a phenotype status of at least one phenotype of a patient;
select from the phenotype engine array at least the first phenotype engine and the second phenotype engine, based at least in part on semantic meaning of the received phenotype query, to execute the received phenotype query on medical data stored in association with the patient, wherein the interface is further configured to receive minimum eligibility requirements of phenotype engines for executing the received phenotype query, and wherein the instructions cause the processor to select the first phenotype engine and the second phenotype engine further by matching the minimum eligibility requirements and profiles of the first phenotype engine and the second phenotype engine in the phenotype engine array;
output, using the interface, results in response to the received phenotype query from the first phenotype engine and the second phenotype engine; and
determine a confidence value associated with the results from each of the first phenotype engine and the second phenotype engine to the user, wherein the results of the first phenotype engine or the second phenotype engine having a higher confidence value are selected.

14. The system of claim 1, wherein the medical data stored in association with the patient comprise records related to some aspect of health of the patient, demographic information of the patient of the patient, and medical history of the patient.

15. The system of claim 14, wherein the medical data stored in association with the patient is stored as part of an electronic medical record (EMR) of the patient.

16. The method of claim 7, wherein the medical data stored in association with the patient comprise records related to some aspect of health of the patient, demographic information of the patient, and medical history of the patient.

17. The system of claim 1, wherein the first entity and the second entity are different entities.

18. The non-transitory computer-readable medium of claim 13, wherein the medical data stored in association with the patient comprise records related to some aspect of health of the patient, demographic information of the patient, and medical history of the patient.

* * * * *